US012233198B2

(12) United States Patent
Locke

(10) Patent No.: US 12,233,198 B2
(45) Date of Patent: Feb. 25, 2025

(54) SYSTEM AND METHOD TO CLEAR CONDUITS OF FLUIDS AFTER INSTILLATION TO A WOUND

(71) Applicant: Solventum Intellectual Properties Company, Maplewood, MN (US)

(72) Inventor: Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 45 days.

(21) Appl. No.: 17/634,495

(22) PCT Filed: Aug. 11, 2020

(86) PCT No.: PCT/IB2020/057543
§ 371 (c)(1),
(2) Date: Feb. 10, 2022

(87) PCT Pub. No.: WO2021/033076
PCT Pub. Date: Feb. 25, 2021

(65) Prior Publication Data
US 2022/0288296 A1 Sep. 15, 2022

Related U.S. Application Data

(60) Provisional application No. 62/889,364, filed on Aug. 20, 2019.

(51) Int. Cl.
*A61M 1/00* (2006.01)
(52) U.S. Cl.
CPC ............ *A61M 1/964* (2021.05); *A61M 1/772* (2021.05); *A61M 1/90* (2021.05); *A61M 1/92* (2021.05);
(Continued)

(58) Field of Classification Search
CPC ........ A61M 1/964; A61M 1/772; A61M 1/90; A61M 1/92; A61M 1/962; A61M 1/966;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for Corresponding Application No. PCT/IB2020/057543 mailed Nov. 17, 2020.
(Continued)

*Primary Examiner* — Sarah Al Hashimi
*Assistant Examiner* — Hans Kaliher

(57) ABSTRACT

A wound therapy system and method for clearing fluids from a conduit includes a wound dressing apparatus, a pneumatic pump, a valve, and a controller. The wound dressing apparatus is fluidly coupled to a wound, the pump, and the valve. The controller is configured to determine a volume of instillation fluid that has been delivered to the wound, to operate the pneumatic pump and the valve to apply a negative pressure to the wound dressing apparatus to purge a first portion of the instillation fluid, and to operate the pneumatic pump and the valve during a purge operation to deliver a volume of air through the wound dressing apparatus that is approximately equal to or greater than the volume of instillation fluid to purge a second portion of the instillation fluid from the wound dressing apparatus.

11 Claims, 8 Drawing Sheets

(52) U.S. Cl.
CPC ............ *A61M 1/962* (2021.05); *A61M 1/966* (2021.05); *A61M 1/982* (2021.05); *A61M 1/83* (2021.05); *A61M 2205/3382* (2013.01)

(58) Field of Classification Search
CPC .................... A61M 1/982; A61M 1/83; A61M 2205/3382; A61M 2205/3344
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2007/0219497 A1* | 9/2007 | Johnson | A61M 1/964 604/131 |
| 2008/0300578 A1* | 12/2008 | Freedman | A61M 1/966 600/587 |
| 2009/0124988 A1* | 5/2009 | Coulthard | A61M 25/003 604/319 |
| 2013/0211318 A1* | 8/2013 | Croizat | A61M 1/77 604/23 |
| 2014/0163491 A1 | 6/2014 | Schuessler et al. | |
| 2015/0080788 A1 | 3/2015 | Blott et al. | |
| 2015/0165182 A1 | 6/2015 | Pratt et al. | |
| 2018/0042521 A1* | 2/2018 | Ryu | A61B 5/742 |
| 2019/0151515 A1* | 5/2019 | Selby | A61M 27/00 |
| 2019/0201595 A1* | 7/2019 | Jardret | A61M 1/962 |
| 2019/0365961 A1* | 12/2019 | Walti | A61M 1/98 |
| 2020/0078499 A1* | 3/2020 | Gadde | A61B 5/447 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2019023311 A1 | 1/2019 |

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

SYSTEM AND METHOD TO CLEAR CONDUITS OF FLUIDS AFTER INSTILLATION TO A WOUND

CROSS-REFERENCE TO RELATED APPLICATIONS

This application claims the benefit of priority to U.S. Provisional Application No. 62/889,364, filed on Aug. 20, 2019, which is incorporated herein by reference in its entirety.

BACKGROUND

The present disclosure relates generally to the management of fluids within conduits for vacuum applications. More specifically, the present disclosure relates to methods and systems for purging instillation fluids from a wound therapy system.

Wound therapy systems including instillation therapy (IT) systems and negative pressure wound therapy (NPWT) systems rely on conduit or flow tubing to transport and receive fluids from a wound site. During instillation, the IT device delivers instillation fluid to the wound site for treatment and to prevent drying of any affected areas. After instillation is complete, the NPWT device applies a negative pressure to the wound site to resume the therapy regimen. The negative pressure forces the instillation fluid into the conduit, which can result in a large pressure drop across the conduit between a pump and the wound site. This large pressure drop may be overcome by increasing the operating speed of the pump, resulting in a large pressure differential between the pump and the wound site. In some instances, the higher negative pressures applied by the pump can be communicated to the wound site, such as when a bolus of instillation fluid suddenly clears from the conduit. In such instances, the NPWT system may be configured to open a valve to vent the wound site to ambient pressure, which may induce dynamic instability in the system. It would be desirable to provide an improved system and method to clear fluids from a conduit following instillation to a wound site during negative pressure wound therapy.

SUMMARY

One implementation of the present disclosure is a wound therapy system. The wound therapy system includes a wound dressing apparatus, a pneumatic pump, a valve, and a controller. The pneumatic pump is fluidly coupled to the wound dressing apparatus and is configured to apply a negative pressure to the wound dressing apparatus. The valve is coupled to the wound dressing apparatus at a location that is upstream of the wound. The controller is communicatively coupled to the pneumatic pump and the valve. The controller is configured to determine a volume of instillation fluid that has been delivered to the wound. The controller is also configured to operate the pneumatic pump and the valve to apply the negative pressure to the wound dressing apparatus to purge a first portion of the instillation fluid from the wound dressing apparatus. The controller is further configured to operate the pneumatic pump and the valve during a purge operation to deliver a volume of air through the wound dressing apparatus that is approximately equal to or greater than the volume of instillation fluid to purge a second portion of the instillation fluid from the wound dressing apparatus.

In any of the above embodiments, the wound therapy system may include a removable fluid canister that is fluidly coupled to the wound dressing apparatus and the pneumatic pump. The removable fluid canister may be configured to receive the instillation fluid from the wound dressing apparatus during the purge operation. In some instances, the wound therapy system also includes a sensor that is fluidly coupled to the removable fluid canister and that is configured to determine a negative pressure of the removable fluid canister. The controller may be communicatively coupled to the sensor and configured to initiate the purge operation based on a determination that the negative pressure of the removable fluid canister is above a predefined purge trigger pressure. Additionally, the controller may be configured to operate the pneumatic pump during the purge operation to maintain the negative pressure of the removable fluidly canister to a value that is approximately equal to a predefined target therapy pressure at the wound. Alternatively, the controller may be configured to operate the pneumatic pump during the purge operation to maintain the negative pressure of the removable fluid canister to a value that is greater than a predefined target therapy pressure at the wound by a predefined threshold.

In any of the above embodiments, the controller may be configured to hold the valve open for a period of time within a range between approximately 5 and 20 seconds during the purge operation.

In some embodiments, the wound dressing apparatus includes a wound dressing and a fluid conduit. The fluid conduit may include at least one sensing lumen and a vacuum lumen. In some aspects, the volume of air is approximately equal to a total volume of the at least one sensing lumen and the vacuum lumen.

In any of the above embodiments, the controller may be configured to repeatedly open and close the valve during the purge operation at a predefined operating frequency. In some embodiments, the valve is a digitally variable, pulse-width-modulation driven valve. The controller may be configured to continuously vary an operating frequency of the valve during the purge operation to provide a gradual increase in flow rate at a beginning of the purge operation and an end of the purge operation.

In any of the above embodiments, the controller may be configured to continuously repeat the purge operation for a predefined number of cycles or for a predefined time period.

In some embodiments, the wound therapy system also includes an instillation fluid canister configured to contain the instillation fluid and an instillation pump configured to deliver the instillation fluid from the instillation fluid canister to the wound dressing apparatus.

In some embodiments, the valve is fluidly coupled to the wound dressing apparatus at a location that is upstream of the wound and the pneumatic pump.

Another implementation of the present disclosure is an apparatus. The apparatus includes a purge control circuit that further includes a memory and a processor. The memory stores machine-readable instructions configured to cause the processor to perform operations. The operations include determining a volume of instillation fluid that has been delivered to a wound through a wound dressing apparatus, operating a pneumatic pump and a valve to apply a negative pressure to the wound dressing apparatus to purge a first portion of the instillation fluid from the wound dressing apparatus, and operating the pneumatic pump and the valve during a purge operation to deliver a volume of air through the wound dressing apparatus that is approximately equal to or greater than the volume of instillation fluid to purge a second portion of the instillation fluid from the wound dressing apparatus.

In some embodiments, the machine readable instructions cause the processor to initiate the purge operation in response to a determination that a negative pressure of a removable fluid canister is above a predefined purge trigger pressure.

Another implementation of the present disclosure is a method of purging a wound dressing apparatus. The method includes providing a volume of instillation fluid to the wound dressing apparatus. The method also includes dwelling, for a first period of time with the instillation fluid contained within the wound dressing apparatus. The method further includes applying, by a pneumatic pump that is fluidly coupled to the wound dressing apparatus and a removable fluid canister, a negative pressure to the wound dressing apparatus to purge a first portion of the instillation fluid from the wound dressing apparatus into the removable fluid canister. The method additionally includes passing, by the pneumatic pump and a valve, a volume of air through the wound dressing apparatus that is approximately equal to or greater than the volume of instillation fluid to purge a second portion of instillation fluid from the wound dressing apparatus into the removable fluid canister.

In some embodiments, the method further includes determining a negative pressure of the removable fluid canister that is fluidly coupled to the wound dressing apparatus and the pneumatic pump, and passing the volume of air through the wound dressing apparatus based on a determination that the negative pressure of the removable fluid canister is above a predefined purge trigger pressure.

In other embodiments, the method of passing the volume of air through the wound dressing apparatus includes determining an open time during which the valve is held in an open position. The method of determining the open time may include identifying a target open time associated with the volume of instillation fluid, and adjusting the open time to equal or substantially equal the target open time.

In some embodiments, the volume of instillation fluid is provided to the wound dressing apparatus by an instillation pump that is fluidly coupled to the wound dressing apparatus.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
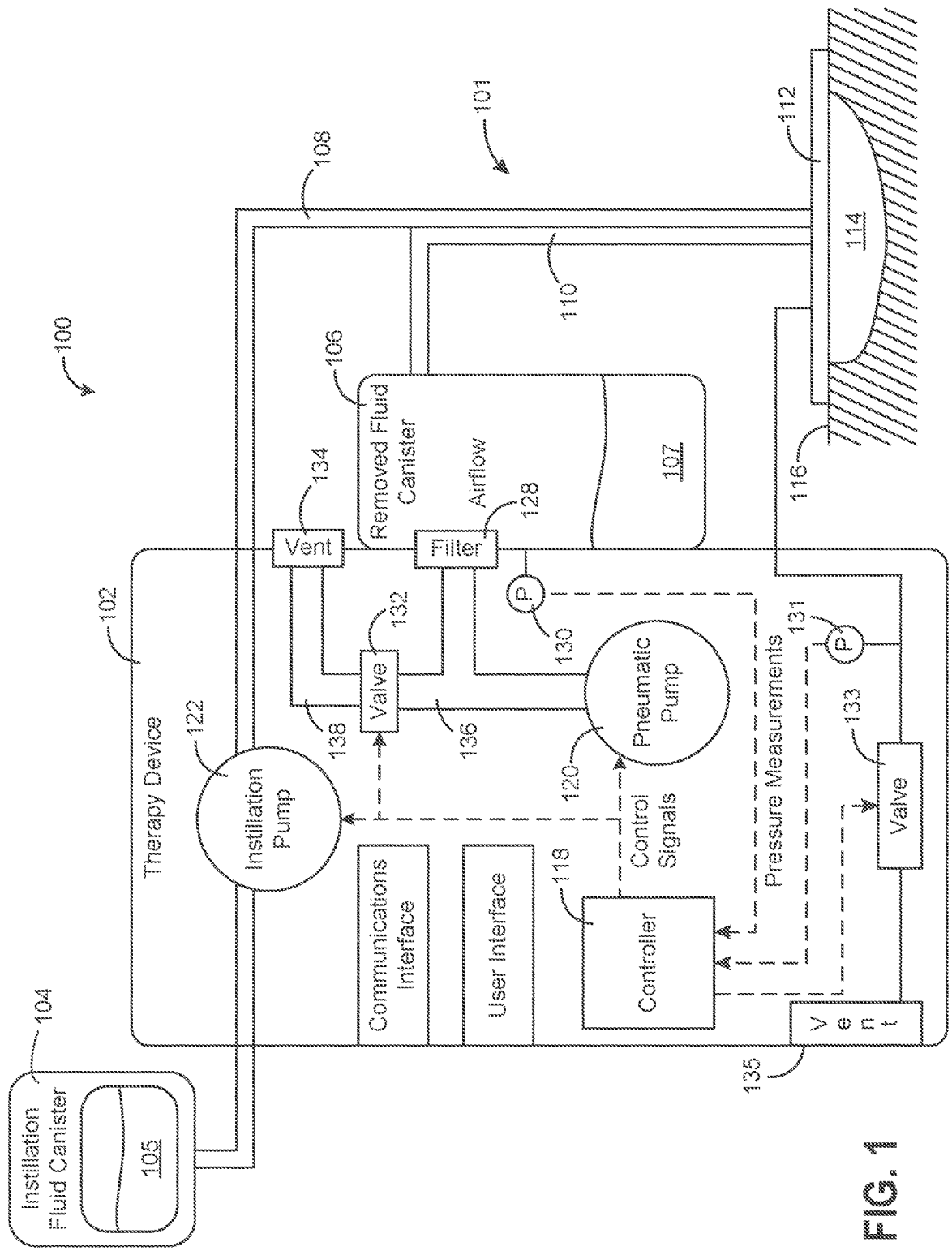
FIG. 1 is a block diagram of a wound therapy system, according to an exemplary embodiment.

Referring generally to the Figures, a wound therapy system and method is provided for actively removing (e.g., purging) liquids (e.g., instillation fluid, wound exudate, etc.) from a wound during negative pressure wound therapy. Specifically, the wound therapy system is configured to remove liquids from the wound through a wound dressing apparatus that is fluidly coupled to the wound. The wound therapy system includes a pneumatic pump and a valve that are both fluidly coupled to the wound dressing apparatus. According to various exemplary embodiments, the valve is located upstream of both the wound and the pneumatic pump. The wound therapy system additionally includes a controller communicatively coupled to the pneumatic pump and the valve. The controller is configured to coordinate operation of the pneumatic pump and the valve to purge the wound dressing apparatus after delivery of an instillation fluid to the wound.

In various exemplary embodiments, the controller is configured to determine a volume of instillation fluid that has been delivered to the wound. The controller may be configured to operate the pneumatic pump and the valve during a purge operation to deliver a volume of air through the wound dressing apparatus that is greater than or equal to the determined volume of instillation fluid. Among other benefits, purging the wound dressing apparatus based on the volume of instillation fluid introduced (into the wound dressing apparatus) reduces the risk of leaving behind any liquids while also minimizing the amount of time required to complete the purge cycle. In some embodiments, the purge cycle may be performed just after the instillation fluid is introduced to the wound site in order to reduce the risk of drying the wound.

In some embodiments, the wound therapy system includes a sensor configured to determine a negative pressure downstream of the wound. Specifically, the sensor may be configured to determine a negative pressure of a removable fluid canister that is disposed between the wound dressing apparatus and the pneumatic pump (e.g., a removable fluid canister configured to receive instillation fluid from the wound dressing apparatus). The controller may be communicatively coupled to the sensor and may be configured to control the pneumatic pump based on information received from the sensor. For example, the controller may be configured to initiate the purge operation based on a determination that the negative pressure of the removable fluid canister is above a predefined threshold (e.g., a purge trigger pressure that indicates a discrepancy between the pressure at the removable fluid canister and the wound, etc.). During the purge operation, information from the sensor may be used by the control the pneumatic pump to maintain the negative pressure of the removable fluid canister above the predefined threshold (e.g., at a purge operating pressure).

In some embodiments, the valve is cycled between an open state and a closed state multiple times by the controller during the purge. Among other benefits, cycling or fluttering the valve reduces system instability and may also allow for pressure monitoring at the wound site during the purge operation to more accurately determine when the instillation liquid has been removable from the wound dressing apparatus. These and other features and advantages of the wound therapy system are described in detail below.

Wound Therapy System Construction

Referring to FIG. 1, a wound therapy system 100 is shown, according to an exemplary embodiment. The wound therapy system 100 is configured to facilitate treatment (e.g., healing) of a wound 114. The wound therapy system 100 is shown to include a therapy device 102 fluidly connected to a wound dressing 112 via instillation tubing 108, sensing tubing 109, and vacuum tubing 110. As used herein, tubing may refer to conduit and/or fluid lines configured to transport fluids to different parts of the wound therapy system 100. The wound dressing 112 may be adhered or sealed to a patient's skin 116 surrounding a wound 114. In various exemplary embodiments, the therapy device 102 is configured to provide negative pressure wound therapy (NPWT) by reducing the pressure at the wound 114. The therapy device 102 can draw a vacuum at the wound 114 (relative to atmospheric pressure) by removing wound exudate, air, and other fluids from the wound 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from the wound 114 may include instillation fluid 105 used to mediate and/or wet the wound 114. Instillation fluid 105 can include, for example, a cleansing fluid, a prescribed fluid, a medicated fluid, an antibiotic fluid, or any other type of fluid which can be delivered to the wound 114 during wound treatment. As shown in FIG. 1, instillation fluid 105 may be held in an instillation fluid canister 104 and controllably dispensed to the wound 114 via instillation tubing 108.

The wound therapy system 100 includes a wound dressing apparatus 101. The wound dressing apparatus 101 is configured to fluidly couple the therapy device 102 to the wound 114. In the exemplary embodiment of FIG. 1, the wound dressing apparatus 101 includes the wound dressing 112, the sensing tubing 109, and the vacuum tubing 110. Specifically, the wound dressing apparatus 101 includes a portion of the sensing tubing 109 that extends between a purge valve 133 and the wound dressing 112, and a portion of the vacuum tubing 110 that extends between a removable fluid canister 106 and the wound dressing 112. The sensing tubing 109 is configured to fluidly couple the one or more sensors to the wound dressing 112 (e.g., wound 114) so that conditions at the wound 114 may be accurately monitored. The vacuum tubing 110 is configured to fluidly couple the wound dressing 112 to an NPWT system that is configured to apply a negative pressure to the wound dressing 112 (and wound 114). In various exemplary embodiments, the sensing tubing 109 and the vacuum tubing 110 are individual lumens (e.g., flow conduits) integrally formed into a single unitary structure (e.g., hose, tube, etc.) that extends between the therapy device 102 and the wound dressing 112. In other embodiments, the number and arrangement of the sensing tubing and/or the vacuum tubing may be different.

As shown in FIG. 1, fluids 107 removed from the wound 114 pass through the vacuum tubing 110 and are collected in the removable fluid canister 106. The removable fluid canister 106 may be a component of the therapy device 102 configured to collect wound exudate and other fluids 107 (e.g., instillation fluid 105) removed from the wound 114. In some embodiments, the removable fluid canister 106 is detachable from the therapy device 102 to allow the canister 106 to be emptied and replaced as needed. A lower portion of the canister 106 may be filled with wound exudate and other fluids 107 removed from the wound 114, whereas an upper portion of the canister 106 may be filled with air. The therapy device 102 can be configured to draw a vacuum within the canister 106 by pumping air out of the canister 106. The reduced pressure within the canister 106 can be translated to the wound dressing 112 and the wound 114 via the vacuum tubing 110 such that the wound dressing 112 and the wound 114 are maintained at approximately the same pressure as canister 106 (or a different pressure depending on the pressure drop through the vacuum tubing 110).

Therapy device 102 is shown to include a pneumatic pump 120, an instillation pump 122, a safety relief valve 132, a purge valve 133, a filter 128, and a controller 118. As shown in FIG. 1, the pneumatic pump 120 is fluidly coupled to the removable fluid canister 106 (e.g., via conduit 136) and is configured to draw a vacuum within canister 106 by pumping air out of canister 106. Pneumatic pump 120 is controlled by a controller 118, as will be described in greater detail below with reference to FIG. 2.

Similarly, instillation pump 122 can be fluidly coupled to instillation fluid canister 104 via instillation tubing 108 and fluidly coupled to wound dressing 112 via instillation tubing 108. The instillation pump 122 is configured to deliver instillation fluid 105 to the wound dressing 112 and the wound 114 by pumping instillation fluid 105 through the instillation tubing 108, as shown in FIG. 1. The instillation pump 122 may also be controlled by controller 118 and/or by a separate, dedicated controller of the therapy device 102.

Filter 128 is positioned between the removable fluid canister 106 and the pneumatic pump 120 (e.g., along conduit 136) such that the air pumped out of the canister 106 passes through the filter 128. The filter 128 is configured to prevent liquid or solid particles from entering the conduit 136 and reaching the pneumatic pump 120. In various exemplary embodiments, the filter 128 includes a bacterial filter that is hydrophobic and/or lipophilic such that aqueous and/or oily liquids will bead on the surface of the filter 128.

As shown in FIG. 1, the safety relief valve 132 can be fluidly connected with the pneumatic pump 120 and the filter 128 via conduit 136. In some embodiments, the safety relief valve 132 is configured to control airflow between the conduit 136 and an environment surrounding the therapy device 102. For example, the safety relief valve 132 may be opened to allow airflow into the conduit 136 via vent 134 and conduit 138, and closed to prevent airflow into the conduit 136 via vent 134 and conduit 138. Among other benefits, the safety relief valve 132 may be used to reduce the risk of damage to the NPWT system due to over-pressurization. The safety relief valve 132 may also be used to rapidly return the NPWT system to ambient pressure when removing or replacing the dressing 112. The safety relief valve 132 is operably coupled to the controller 118 and may be opened and closed by controller 118.

The purge valve 133 is fluidly coupled to the sensing tubing 109. The purge valve 133 is configured to control airflow between the sensing tubing 109 and the environment surrounding the therapy device 102. For example, the purge valve 133 may be opened to allow airflow into the sensing tubing 109 via vent 135. During operation (e.g., when the pneumatic pump 120 is activated), air entering the sensing tubing 109 through the purge valve 133 is directed through the sensing tubing 109 and toward the wound dressing 112. At the wound dressing 112, the air is redirected through the vacuum tubing 110 as a result of the negative pressure applied to the removable fluid canister 106 by the pneumatic pump 120. As the air moves along the sensing tubing 109 and vacuum tubing 110, it forces liquids contained within the wound dressing apparatus 101, including wound exudate, instillation fluid 105, and/or other fluids 107 out of the wound dressing apparatus 101, and into the removable fluid canister 106, thereby purging the wound dressing apparatus 101 of any entrained liquids.

The safety relief valve 132 and the purge valve 133 may be electronically controlled solenoid valves. The safety relief valve 132 may be the same or similar to the purge valve 133. In various exemplary embodiments, the purge valve 133 is configured to regulate the flow rate of air through the vent 135 to prevent a sudden crash (e.g., reduction) in negative pressure at the wound 114 (e.g., an abrupt increase in static pressure at the wound 114) when the purge valve 133 is activated (e.g., opened). For example, the purge valve 133 may be cycled between an open and closed state at a predefined operating frequency by the controller 118 to gradually reduce the negative pressure at the start of a purge cycle. In some embodiments, the purge valve 133 is a digitally variable, pulse-width-modulation (PWM) driven valve which functions as a digitally variable orifice that can be tuned to provide a digital and profiled rate of pressure decay at the wound 114. In other embodiments, the purge valve 133 may include a plurality of valves arranged in parallel to selectively vary the air flow rate into the sensing tubing 109.

The therapy device 102 additionally includes a plurality of sensors configured to monitor operating conditions in different parts of the wound therapy system 100. In the exemplary embodiment of FIG. 1, the therapy device 102 includes a plurality of pressure sensors. A first pressure sensor 130 of the plurality of pressure sensors is coupled to the removable fluid canister 106 and is configured to measure a pressure (e.g., static pressure) of the removable fluid canister 106. A second pressure sensor 131 of the plurality of pressure sensors is coupled to the sensing tubing 109 at a location between the purge valve 133 and the wound dressing 112. The second pressure sensor 131 is configured to measure a pressure (e.g., static pressure) at the wound 114 (e.g., a wound site to which the wound dressing 112 is coupled). The plurality of pressure sensors may be communicatively coupled to the controller 118 such that pressure measurements collected by the plurality of pressure sensors may be communicated to the controller 118. The controller 118 uses the pressure measurements to ensure that the wound 114 is maintained at a target negative pressure and/or to determine whether a purge operation is required to remove liquids from the wound dressing apparatus 101, as will be further described below with reference to FIG. 2.

Controller

Figure 2:
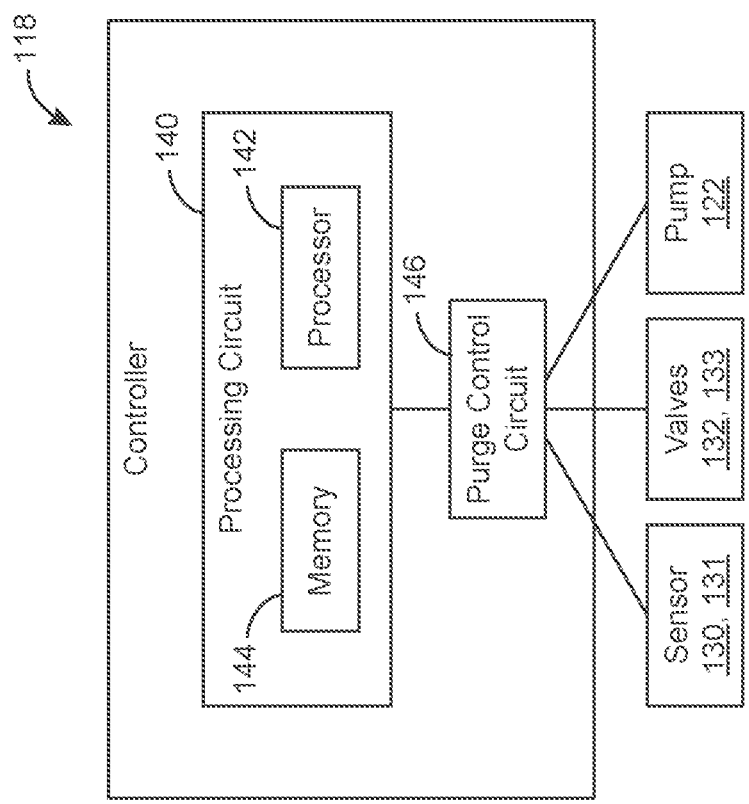
FIG. 2 is a block diagram of a controller for a wound therapy system, according to an exemplary embodiment.

Referring now to FIG. 2, a block diagram illustrating the controller 118 in greater details is shown, according to an exemplary embodiment. In other embodiments, the controller 118 may include additional, fewer, and/or different components. The controller 118 is shown to include a processing circuit 140 including a processor 142 and memory 144. The processor 142 may be a general purpose or specific purpose processor, an application specific integrated circuit (ASIC), one or more field programmable gate arrays (FPGAs), a group of processing components, or other suitable processing components. The processor 142 is configured to execute computer code or instructions stored in memory 144 or received from other computer readable media (e.g., CDROM, network storage, a remote server, etc.).

Memory 144 may include one or more devices (e.g., memory units, memory devices, storage devices, etc.) for storing data and/or computer code for completing and/or facilitating the various processes described in the present disclosure. Memory 144 may include random access memory (RAM), read-only memory (ROM), hard drive storage, temporary storage, non-volatile memory, flash memory, optical memory, or any other suitable memory for storing software objects and/or computer instructions. Memory 144 may include database components, object code components, script components, or any other type of information structure for supporting the various activities and information structures described in the present disclosure. Memory 144 may be communicably connected to the processor 142 via processing circuit 140 and may include computer code for executing (e.g., by the processor 142) one or more processes described herein. When the processor 142 executes instructions stored in memory 144, the processor 142 generally configures the controller 118 (and more particularly processing circuit 140) to complete such activities.

The controller 118 is shown to include a purge control circuit 146. The purge control circuit 146 may be configured to determine a volume of instillation fluid 105 that has been delivered to the wound 114 (see also FIG. 1) and to control the purge operation to remove at least the determined volume of instillation fluid 105 from the wound dressing apparatus 101. In various exemplary embodiments, the purge control circuit 146 is configured to determine a maximum volume of instillation fluid 105 that may be present within the wound dressing apparatus 101. For example, the purge control circuit 146 may be configured to determine a total volume of the wound dressing apparatus 101 by accessing a look-up table stored in memory 144. The look-up table may include a list of target therapy pressures at the wound 114 and a corresponding list of valve operating times (e.g., periods) for the purge valve 133. The operating times may be open times for the purge valve 133 (e.g., durations of time during which the purge valve 133 is operated in an open state) that are required to completely purge a volume of air through the wound dressing apparatus 101 that is greater than or equal to the total volume of the wound dressing apparatus 101. The purge control circuit 146 may be configured to determine a valve operating time from the look-up table based on a target therapy pressure at the wound 114 (e.g., a target therapy pressure input by a user via a user interface on the therapy device 102 or stored in memory 144).

In some embodiments, the purge control circuit 146 is configured to determine a valve operating time based on a predefined purge operating pressure that is applied to the removable fluid canister 106. The predefined purge operating pressure may be greater than the target therapy pressure to ensure that the liquids (e.g., instillation fluid 105, wound exudate, and other fluids 107) can be carried up through the vacuum tubing 110 (see also FIG. 1). The purge control circuit 146 may be configured to compare the target therapy pressure with the predefined purge operating pressure at the start of the purge operation and to adjust the negative pressure if needed. For example, the purge operating pressure may be 125 mmHg. In scenarios where the target therapy pressure is less than the purge operating pressure (e.g., 75 mmHg), the purge control circuit 146 may readjust the speed of the pneumatic pump 120 to increase the negative pressure within the removable fluid canister 106 during the purge operation (e.g., to a value that is approximately equal to the purge operating pressure). Conversely, in scenarios where the target therapy pressure is greater than or equal to the purge operating pressure, the purge control circuit 146 will operate the pneumatic pump 120 to maintain the negative pressure within the removable fluid canister 106 at a value that is approximately equal to the target therapy pressure.

The list of valve operating times stored in memory 144 may be determined by the purge control circuit 146 based on a total volume of the wound dressing apparatus 101. Specifically, the valve operating times may be those required to flush a volume of air equal to the total volume of the wound dressing apparatus 101 through the sensing tubing 109 (e.g., the portion of the sensing tubing 109 between the purge valve 133 and the wound dressing 112) and the vacuum tubing 110 (e.g., the portion of the vacuum tubing 110 between the wound dressing 112 and the removable fluid canister 106). The valve operating times will vary depending on the negative pressure within the removable fluid canister 106 during the purge operation. The purge control circuit 146 may be configured to determine the total volume of the wound dressing apparatus 101 based on user inputs (e.g., via a user interface on the therapy device 102). For example, the purge control circuit 146 may be configured to determine the total volume based on the diameter and length of at least one of the sensing tubing 109 and the vacuum tubing 110. The times required to flush the volume of air through the wound dressing apparatus 101 (e.g., the purge times) may also be determined based on a type of filter 128 and a flow area through the filter 128, and/or a calculation of the likely range of wound exudate, fluid viscosity, and the flow restriction through the wound dressing 112 (which together may be more than a theoretical purge time for a gas only volume). Alternatively, or in combination, the purge control circuit 146 may be configured to determine the purge times based directly on an instilled fluid volume provided to the purge control circuit 146 by an installation control circuit (not shown) or based on a user specified value of the instilled fluid volume stored in memory 144.

In various exemplary embodiments, the purge control circuit 146 may be configured to calculate the required purge time directly based on user inputs, tubing data, and/or operating data stored in memory 144. In an exemplary embodiment, the air flow rate through the sensing tubing 109 (see also FIG. 1) is approximately 860 cc/min (14.3 cc/second). The vacuum tubing 110 is approximately 2.8 m in length and has a diameter of approximately 3.55 mm. For the purposes of this example, the volume of the sensing tubing 109 can be assumed to be negligible relative to the volume of the vacuum tubing 110. Based on these parameters, the required purge time of air through the wound dressing apparatus 101 (e.g., the required valve open time) is approximately 2 s. In some embodiments, the purge control circuit 146 may be configured to double the required purge time (e.g., 4 s) or increase the overall purge time by another scaling factor to ensure that all liquids are removed from the wound dressing apparatus 101 during the purge operation.

As shown in FIG. 2, the purge control circuit 146 is configured to operate the pneumatic pump 120 and at least one of the safety relief valve 132 and the purge valve 133 by generating and providing control signals to the pneumatic pump 120 and/or the valves 132 and 133. The control signals provided to the pneumatic pump 120 can cause the pneumatic pump 120 to activate, deactivate, or achieve a variable capacity or speed (e.g., operated at half speed, operate at full speed, etc.). Similarly, the control signals provided to the valves 132 and 133 can cause the valves 132 and 133 to open, close, or to cycle between an open and closed state at a predefined operating frequency.

In some embodiments, the purge control circuit 146 is configured to change the operating frequency (e.g., cycling frequency) of the valves 132 and 133 during operation. For example, the operating frequency of the purge valve 133 may be controlled/varied during a purge cycle to gradually increase a flow rate of air into the sensing tubing 109 (see also FIG. 1) at a beginning of the purge operation and/or to gradually reduce the flow rate of air into the sensing tubing 109 at an end of the purge operation. Among other benefits, gradually transitioning the purge valve 133 between a closed state and an open state prevents a rapid increase or decrease in negative pressure at the wound 114. For example, the purge control circuit 146 may transmit a first control signal to the purge valve 133 to operate the purge valve 133 at a first operating frequency to gradually introduce air into the wound dressing apparatus 101. After a first period of time, the purge control circuit 146 may transmit a second control signal to the purge valve 133 to maintain the purge valve 133 in a fully open state (e.g., position) to allow air to pass through the purge valve 133 unimpeded. Near the end of the purge operation, the purge control circuit 146 may transmit a third control signal to the purge valve 133 to again operate the purge valve 133 at the first operating frequency to gradually reduce the flow rate of air into the sensing tubing 109.

In other exemplary embodiments, the purge control circuit 146 may be configured to continuously vary the operating frequency of the purge valve 133 during the purge operation, for example, by using a PWM driven purge valve 133. Among other benefits, cycling or fluttering the purge valve 133 at the beginning of the purge operation and at the end of the purge operation can reduce dynamic instability in the control system (e.g., instability relating to rapid changes in negative pressure in at least one of the wound 114 and the removable fluid canister 106).

As shown in FIG. 2, the controller 118 (e.g., the purge control circuit 146) is communicatively coupled to the plurality of sensors and is configured to take action based on information (e.g., sensor data) received from each of the plurality of sensors. In various exemplary embodiments, the purge control circuit 146 is configured to initiate the purge operation based on information from at least one of the first pressure sensor 130 (e.g., the pressure sensor that is coupled to the removable fluid canister 106) and the second pressure sensor 131 (e.g., the pressure sensor that is coupled to the sensing tubing 109). For example, the purge control circuit 146 may be configured to initiate the purge operation based on a determination that the negative pressure of the removable fluid canister 106 is above a predefined purge trigger pressure (e.g., a negative pressure that is much greater than a target therapy pressure at the wound 114), which can occur when a volume of liquid accumulates within the vacuum tubing 110. Alternatively, or in combination, the purge control circuit 146 may be configured to initiate the purge operation based on a determination that a difference between the negative pressure in the removable fluid canister 106 and the negative pressure at the wound 114 exceeds a predefined threshold.

The purge control circuit 146 may also be configured to automatically control the pneumatic pump 120 during the purge operation based on sensor data; for example, to maintain the negative pressure of the removable fluid canister 106 to a value that is greater than a predefined target therapy pressure (e.g., a purge operating pressure stored in memory 144). Among other benefits, using automatic pump control based on sensor data ensures that a target therapy pressure is maintained at the wound 114 (e.g., that performance targets can be achieved regardless of the additional hydraulic head caused by liquid in the vacuum tubing 110).

In various exemplary embodiments, the purge control circuit 146 may be configured to repeat the purge operation for a predefined number of cycles and/or for a predefined time period to ensure that all liquids such as wound exudate, instillation fluid 105, and other fluids 107 are fully removed from the wound dressing apparatus 101 (see also FIG. 1). The predefined number of cycles and/or predefined time period may be input by a user (e.g., via user interface on the therapy device 102) or otherwise stored in memory 144 (e.g., during manufacturing of the therapy device 102).

Method of Purging a Wound Dressing Apparatus

Figure 3:
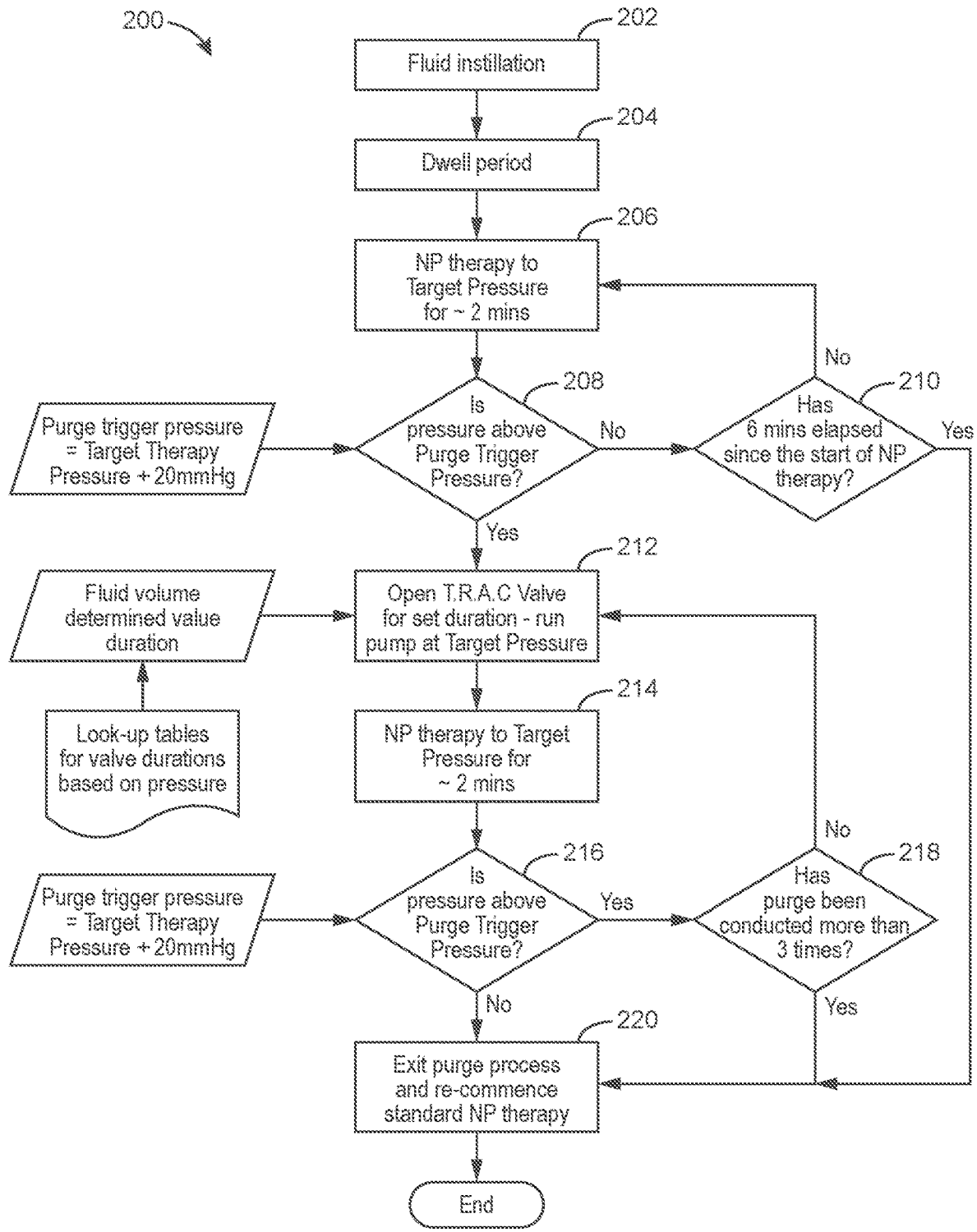
FIG. 3 is a flow diagram of a method of purging a wound dressing apparatus for a wound therapy system, according to an exemplary embodiment.
Figure 4:
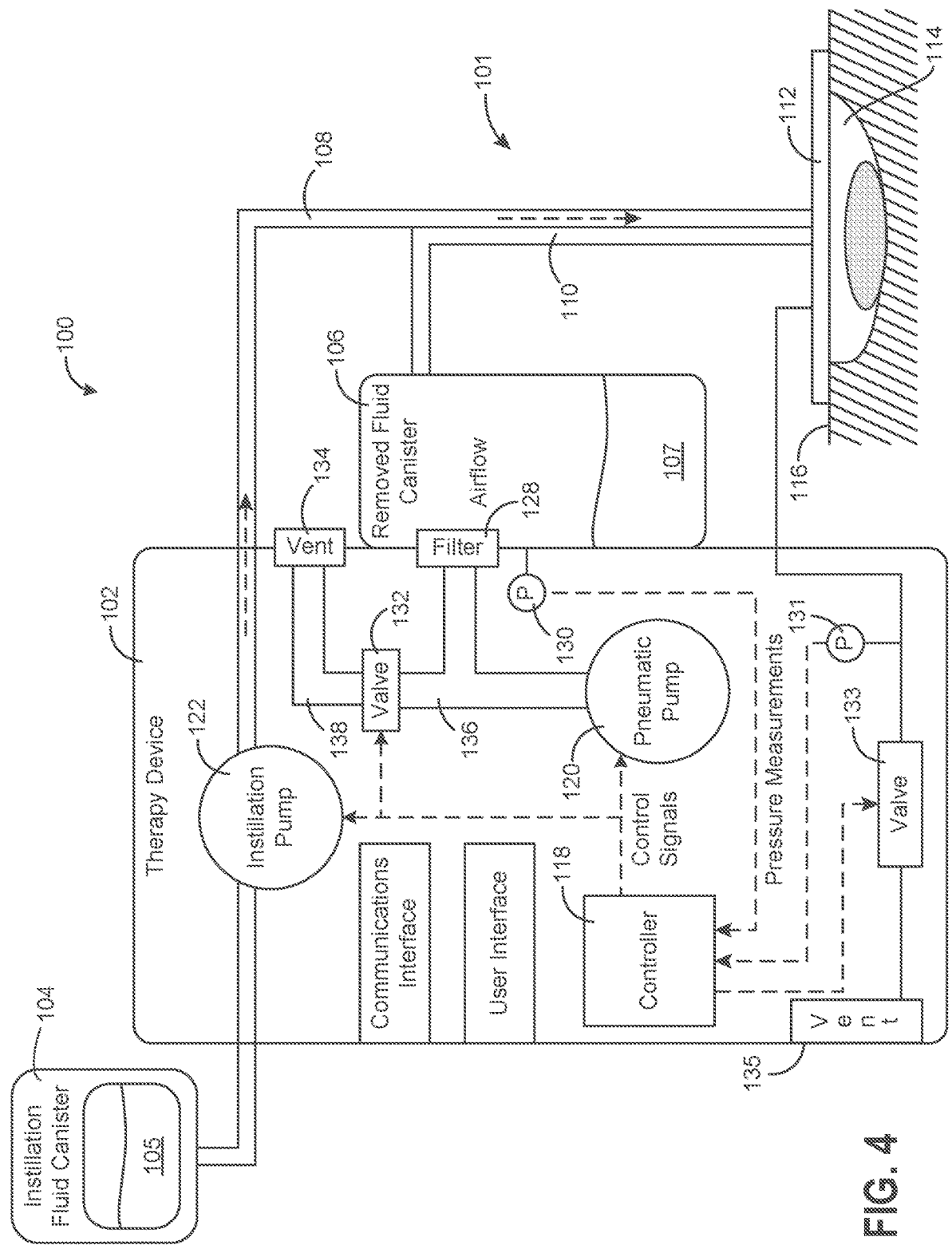
FIG. 4 is a block diagram of the wound therapy system of FIG. 1 in a first mode of operation.

Referring to FIG. 3, a flow diagram of a method 200 of purging a wound dressing apparatus is shown, according to an exemplary embodiment. The method 200 may be implemented by a wound therapy system to remove liquids (e.g., wound exudate, instillation fluid 105, and other fluids) from a wound dressing apparatus. The method 200 may be applied by the wound therapy system directly after instillation and/or routinely (e.g., periodically) during a treatment regimen by an NPWT system. The wound therapy system may be the same or similar to the wound therapy system 100 of FIGS. 1-2. For simplicity, similar numbering will be used to identify similar components. At 202, a volume of instillation fluid 105 is provided to the wound dressing apparatus 101 by an instillation pump 122. Block 202 is illustrated schematically in FIG. 4. As shown in FIG. 4, block 202 includes passing the volume of instillation fluid 105 from the instillation fluid canister 104, through the instillation tubing 108, and into the wound 114 (via the wound dressing 112). Block 202 may continue until the wound 114 is completely filled with instillation fluid 105. Alternatively, the volume of instillation fluid 105 provided to the wound 114 may be determined based on user inputs to the therapy device 102 or may be a predetermined value (e.g., stored in memory 144).

Figure 5:
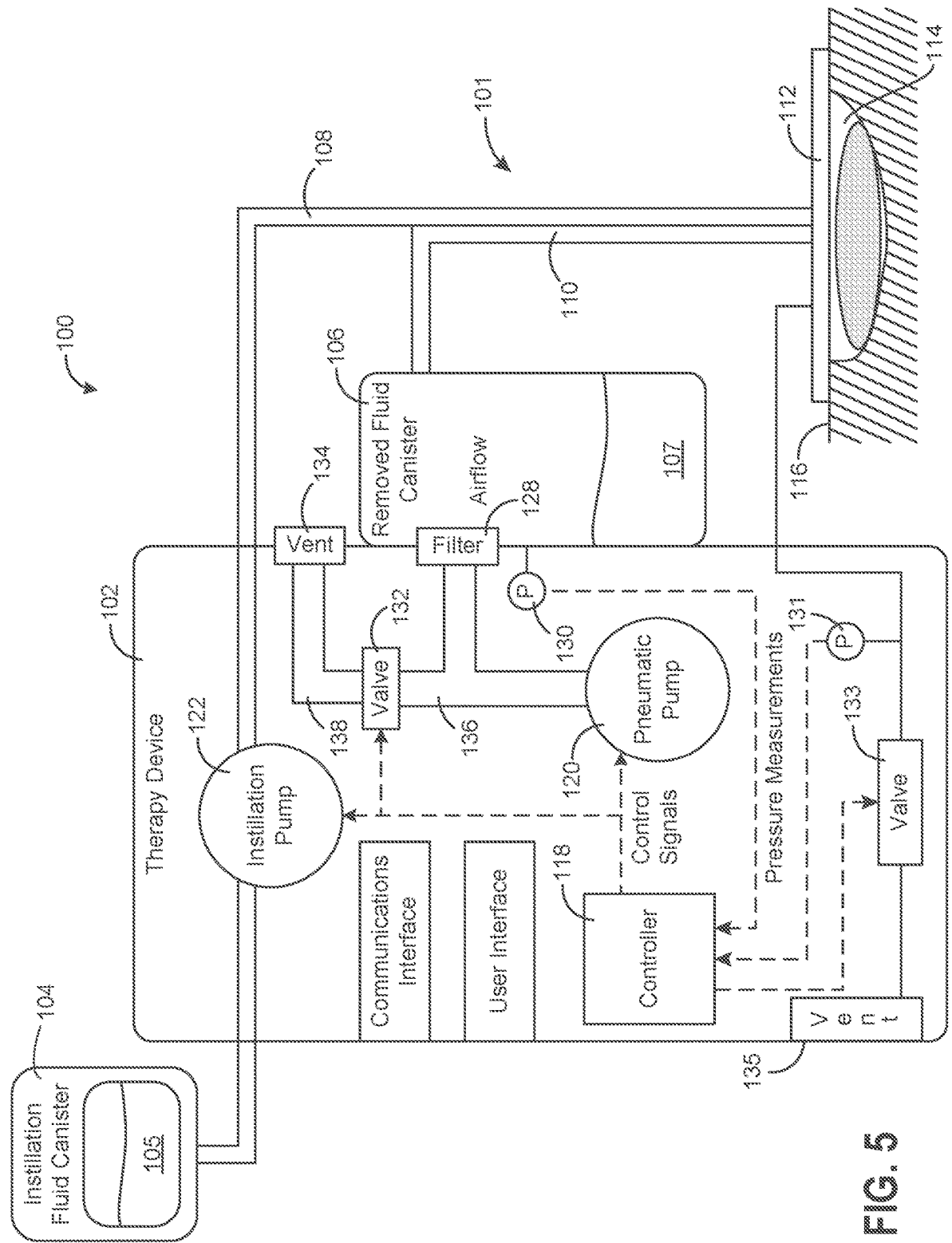
FIG. 5 is a block diagram of the wound therapy system of FIG. 1 in a second mode of operation.
Figure 6:
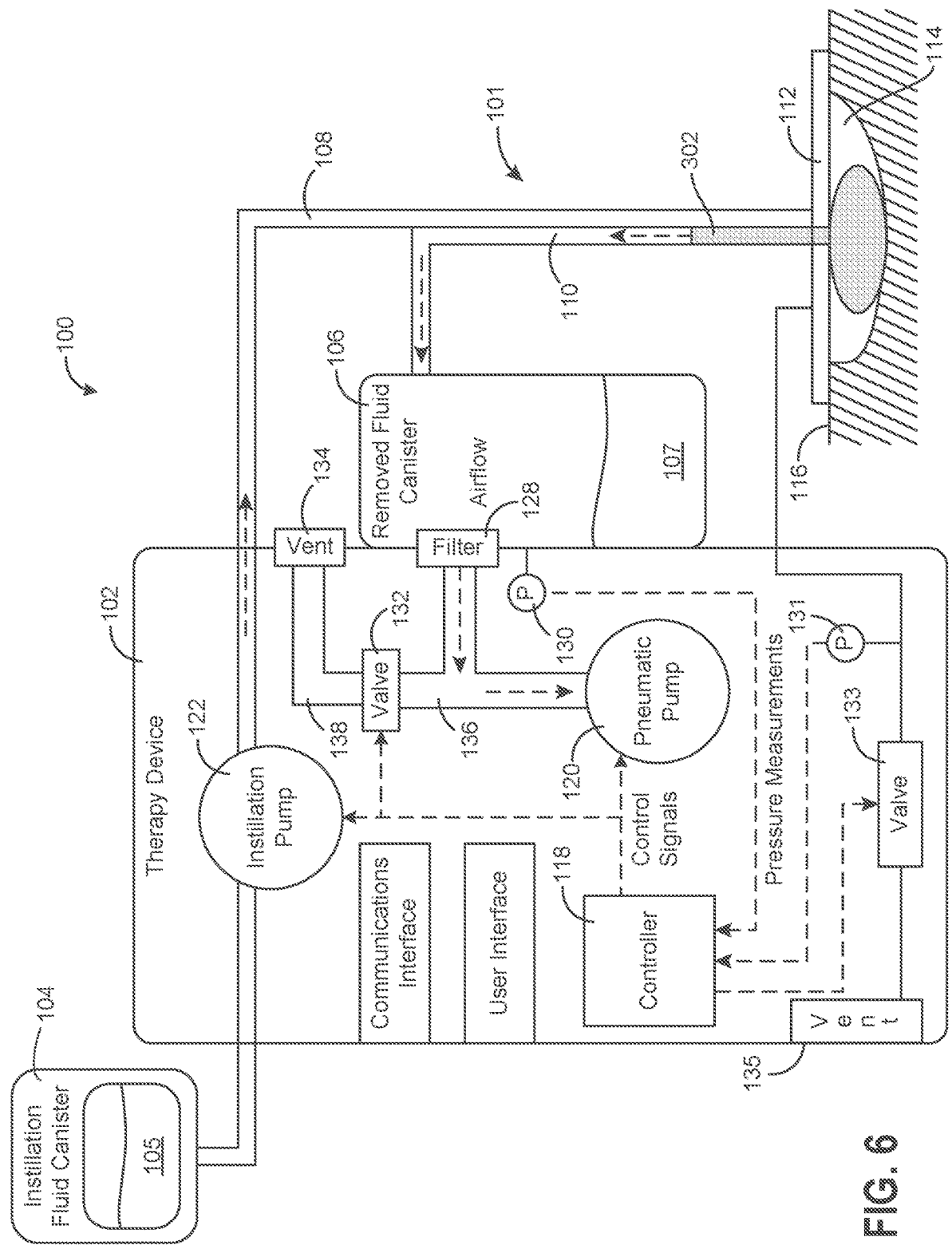
FIG. 6 is a block diagram of the wound therapy system of FIG. 1 in a third mode of operation.

At 204, the wound therapy system 100 dwells (e.g., pauses, rests, etc.) with the instillation pump 122 and pneumatic pump 120 in a deactivated state (e.g., shut down, turned off) for a first period of time. Block 204 is shown schematically in FIG. 5. During the dwell operation, instilled fluid 105 is allowed to remain within the wound 114. At 206, a pneumatic pump 120 applies a negative pressure to the wound dressing apparatus 101 to purge a first portion 302 of the instillation fluid 105 from the wound dressing apparatus 101 and into a removable fluid canister 106. Block 206 is shown schematically in FIG. 6. During block 206, other fluids such as wound exudate may also be removed from the wound 114 and delivered into the removable fluid canister 106. Block 206 may include operating the pneumatic pump 120, in response to a control signal from a controller 118, to apply the negative pressure for a predefined period of time (e.g., 2 minutes or another period of time that is required to achieve steady-state conditions within the wound dressing apparatus 101). Block 206 may additionally include operating the pneumatic pump 120 based on sensor data from the second pressure sensor 131. Specifically, block 206 may include operating the pneumatic pump 120 to automatically increase the negative pressure applied by the pneumatic pump 120 to the removable fluid canister 106 to offset any additional head height associated with remaining liquids in the vacuum tubing 110 (e.g., such that the wound 114 is maintained at the target therapeutic pressure).

At 208, a controller 118 compares the negative pressure of the removable fluid canister 106 (e.g., via first pressure sensor 130) with a purge trigger pressure to determine whether any liquids remain in the wound dressing apparatus 101. The purge trigger pressure may be equal to a target therapy pressure at the wound 114 plus a predefined offset (e.g., 20 mmHg, or another suitable offset pressure indicative of liquid within the wound dressing apparatus 101). In a scenario where the negative pressure of the removable fluid canister 106 is below the purge trigger pressure, the method 200 proceeds to block 208. At 210, the controller 118 compares an amount of time since the start of the NPWT regimen (e.g., since the start of block 206) to a predefined fluid check period. The predefined fluid check period is a period of time during which the therapy device 102 continually checks to see if the negative pressure in the removable fluid canister 106 has exceeded the purge trigger pressure. It should be understood that the negative pressure in the removable fluid canister 106 may change over time due to the introduction of wound exudate into the vacuum tubing 110 and/or other parts of the wound dressing apparatus 101 (e.g., from the wound 114). In a scenario where the negative pressure in the removable fluid canister 106 remains below the purge trigger pressure throughout the fluid check period, the method 200 proceeds to block 220, and the controller 118 proceeds to implement a continuous NPWT regimen.

Figure 7:
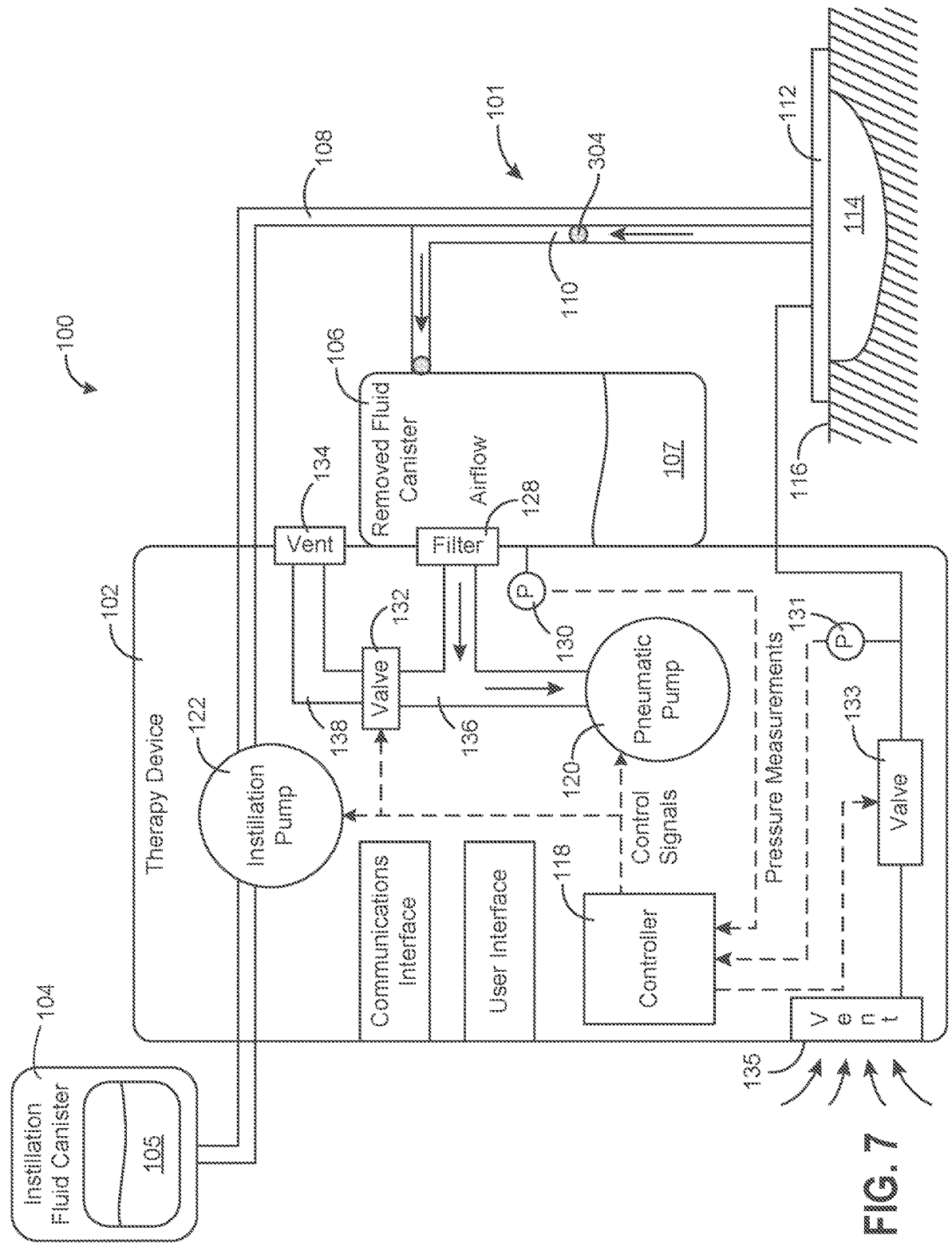
FIG. 7 is a block diagram of the wound therapy system of FIG. 1 in a fourth mode of operation.

In the event the negative pressure of the removable fluid canister 106 exceeds the purge trigger pressure within the fluid check period, the method 200 proceeds to block 212. At 212, the controller 118 activates the purge valve 133 (while operating the pneumatic pump 120) to pass a volume of air through the wound dressing apparatus 101 that is greater than or equal to the volume of instillation fluid 105 provided in block 202. Block 212 includes purging a second portion 304 of the instillation fluid 105 from the wound dressing apparatus 101 into the removable fluid canister 106. Block 212 is shown schematically in FIG. 7. Block 212 may additionally include determining, by the controller 118 (e.g., the purge control circuit 146 of FIG. 2), a valve open time (e.g., duration) during which the purge valve 133 is held in an open position. In some embodiments, determining the open time includes accessing a look-up table from memory 144 that includes a list of open times. The list of open times may be a function of different operating parameters such as the negative pressure in the removable fluid canister 106, the volume of the wound dressing apparatus 101, the volume of instillation fluid 105 delivered to the wound 114, and/or other factors. Block 212 may include adjusting the open time to equal or substantially equal the target open time. Block 212 may further include sending a control signal to the pneumatic pump 120 to increase the negative pressure in the removable fluid canister 106 to the purge operating pressure (e.g., a value greater than the target therapy pressure to ensure the pressure is adequate to remove liquids from the vacuum tubing 110).

At 214, the controller 118 operates the purge valve 133 and the pneumatic pump 120 to maintain the negative pressure at the wound 114 at the target therapy pressure. Block 214 may include closing the purge valve 133 to prevent any additional purging of the wound dressing apparatus 101. Block 214 may additionally include adjusting the operating speed of the pneumatic pump 120 to reduce the negative pressure in the removable fluid canister 106 (e.g., to reduce the negative pressure to the target therapy pressure or to another value that is lower than the purge operating pressure).

Figure 8:
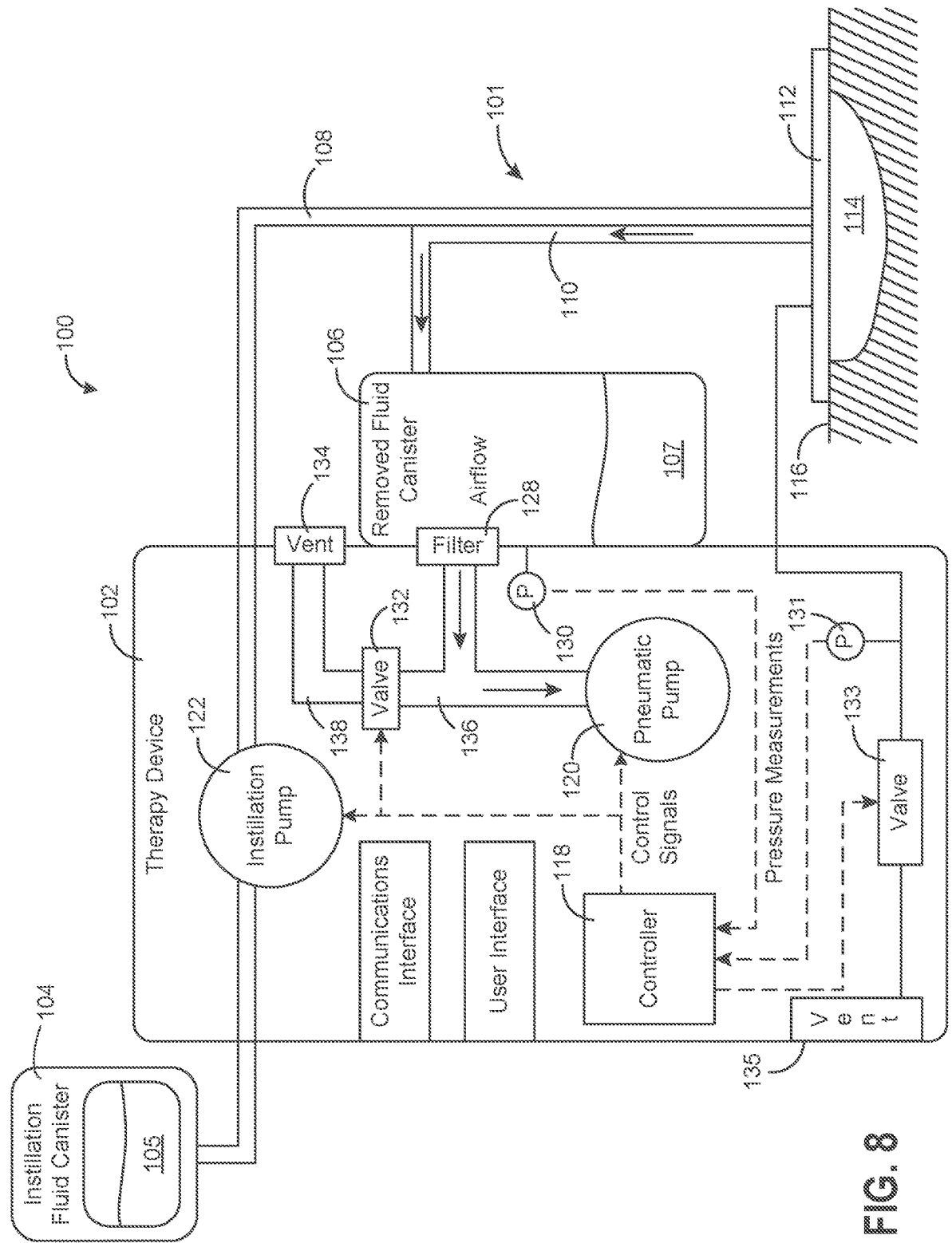
FIG. 8 is a block diagram of the wound therapy system of FIG. 1 in a fifth mode of operation.

At 216, the controller 118 determines whether the negative pressure in the removable fluid canister 106 is greater than the purge trigger pressure. In a scenario where the negative pressure in the removable fluid canister 106 exceeds the purge trigger pressure, the method 200 returns to block 212 and repeats the purge operation. Block 216 may additionally include recording a number of purge cycles. At 218, the controller 118 compares the number of purge cycles with a predefined threshold number of cycles. In a scenario where the number of purge cycles exceeds the predefined number of cycles, or in a scenario where the negative pressure within the removable fluid canister 106 is less than the purge trigger pressure (after a purge), the method 200 proceeds to block 220 in which the standard NPWT regime is resumed. Block 220 is shown schematically in FIG. 8. In other embodiments, the method 200 of FIG. 3 may include additional, fewer, and/or different operations.

The method 200 described in the exemplary embodiment of FIG. 3 should not be considered limiting. Many alternatives are possible without departing from the inventive concepts disclosed herein. For example, the purge operation may also be performed periodically during the normal NPWT regimen (e.g., after a bulk of the instillation fluid 105 has been removed and the negative pressure within the removable fluid canister 106 is below the purge trigger pressure). Among other benefits, repeating the purge cycle periodically during treatment may also help to prevent the buildup of wound exudate that might otherwise clog the vacuum tubing 110 and/or interfere with accurate pressure measurements of the wound 114. In some embodiments, the purge operation may include increasing the open times for the purge valve 133 to a longer duration and/or reapplying the purge operation more frequently throughout the NPWT regimen. For example, the wound therapy system 100 may be configured to increase open times for the purge valve 133 to 5-10 second intervals every 2 minutes directly after an instillation/dwell operation for a total time of 8-10 minutes or another suitable time to aid with fluid removal. As described above, during the purge operation, the controller 118 may operate the pneumatic pump 120 to apply a higher negative pressure to the removable fluid canister 106 (e.g., greater than a target therapy pressure at the wound 114) to ensure that enough pressure is provided to the return fluid canister 106 to overcome any head in the vacuum tubing 110 due to trapped liquids.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A wound therapy system, comprising:
a wound dressing apparatus fluidly coupled to a wound;
a pneumatic pump fluidly coupled to the wound dressing apparatus and configured to apply a negative pressure to the wound dressing apparatus;
a removable fluid canister coupled to the wound dressing apparatus and the pneumatic pump;
a sensor fluidly coupled to the removable fluid canister and configured to determine a negative pressure of the removable fluid canister;
a valve fluidly coupled between an ambient environment and the wound dressing apparatus at a location that is upstream of the wound, the valve being configured to allow airflow between ambient environment and the wound when the valve is open; and
a controller communicatively coupled to the pneumatic pump, the sensor, and the valve and configured to:
determine a volume of instillation fluid that has been delivered to the wound;
operate the pneumatic pump and the valve to apply the negative pressure to the wound dressing apparatus to purge a first portion of the instillation fluid from the wound dressing apparatus;
initiate a purge operation based on a determination that the negative pressure of the removable fluid canister is above a predefined purge trigger pressure; and
operate the pneumatic pump and the valve during the purge operation to deliver a volume of air from the ambient environment through the wound dressing apparatus that is approximately equal to or greater than the volume of instillation fluid to purge a second portion of the instillation fluid from the wound dressing apparatus.

2. The wound therapy system of claim 1, wherein the removable fluid canister is configured to receive the instillation fluid from the wound dressing apparatus during the purge operation.

3. The wound therapy system of claim 1, wherein during the purge operation the controller is configured to operate the pneumatic pump to maintain the negative pressure of the removable fluid canister to a value that is approximately equal to a predefined target therapy pressure at the wound.

4. The wound therapy system of claim 1, wherein during the purge operation the controller is configured to operate the pneumatic pump to maintain the negative pressure of the removable fluid canister to a value that is greater than a predefined target therapy pressure at the wound by a predefined threshold.

5. The wound therapy system of claim 1, wherein during the purge operation the controller is configured to hold the valve open for a period of time within a range between approximately 5 and 20 seconds.

6. The wound therapy system of claim 1, wherein the wound dressing apparatus comprises a wound dressing and a fluid conduit, wherein the fluid conduit comprises at least one sensing lumen and a vacuum lumen, and wherein the volume of air is approximately equal to a total volume of the at least one sensing lumen and the vacuum lumen.

7. The wound therapy system of claim 1, wherein during the purge operation the controller is configured to repeatedly open and close the valve at a predefined operating frequency.

8. The wound therapy system of claim 1, wherein the valve is a digitally variable, pulse-width-modulation driven valve, and wherein during the purge operation the controller is configured to continuously vary an operating frequency of the valve to provide a gradual increase in flow rate at a beginning of the purge operation and an end of the purge operation.

9. The wound therapy system of claim 1, wherein the controller is configured to continuously repeat the purge operation for a predefined number of cycles or for a predefined time period.

10. The wound therapy system of claim 1, further comprising an instillation fluid canister configured to contain the instillation fluid and an instillation pump configured to deliver the instillation fluid from the instillation fluid canister to the wound dressing apparatus.

11. The wound therapy system of claim 1, wherein the valve is fluidly coupled to the wound dressing apparatus at a location that is upstream of the wound and the pneumatic pump.

* * * * *